US006518291B1

(12) United States Patent
Saunders et al.

(10) Patent No.: US 6,518,291 B1
(45) Date of Patent: Feb. 11, 2003

(54) INHIBITORS OF IMPDH ENZYME

(75) Inventors: Jeffrey O. Saunders, Acton, MA (US); David M. Armistead, Sudbury, MA (US); Michael C. Badia, Bedford, MA (US); Randy S. Bethiel, Cambridge, MA (US); Catherine A. Frank, Langhorne, PA (US); Doug Naegele, Washington, DC (US); Perry M. Novak, Milford, MA (US); David A. Pearlman, Arlington, MA (US); Steven M. Ronkin, Watertown, MA (US)

(73) Assignee: Vertex Pharmaceuticals, Incorporated, Cambridge, MA (US)

( * ) Notice: Subject to any disclaimer, the term of this patent is extended or adjusted under 35 U.S.C. 154(b) by 0 days.

(21) Appl. No.: 09/395,798

(22) Filed: Sep. 14, 1999

Related U.S. Application Data

(63) Continuation-in-part of application No. PCT/US98/04932, filed on Mar. 13, 1998, which is a continuation-in-part of application No. 08/816,764, filed on Mar. 14, 1997, now Pat. No. 5,932,600.
(60) Provisional application No. 60/042,443, filed on Mar. 28, 1997.

(51) Int. Cl.$^7$ .................. A61K 31/136; A61K 31/4168; C07C 211/45; C07D 235/30
(52) U.S. Cl. .................. 514/367; 514/375; 514/388; 514/415; 514/443; 514/452; 514/466; 514/470; 514/657; 548/161; 548/222; 548/307.4; 548/483; 549/57; 549/439; 549/467; 564/428
(58) Field of Search .................. 514/367, 375, 514/388, 415, 443, 470, 452, 466, 657; 548/161, 222, 307.4, 483; 549/57, 467, 439; 564/428

(56) References Cited

U.S. PATENT DOCUMENTS

| | | | |
|---|---|---|---|
| 4,405,644 A | 9/1983 | Kabbe et al. | 424/322 |
| 5,380,879 A | 1/1995 | Sjogren | 549/310 |
| 5,444,072 A | 8/1995 | Patterson et al. | 514/320 |
| 5,536,747 A | 7/1996 | Patterson et al. | 514/470 |
| 5,807,876 A | 9/1998 | Armistead et al. | 514/374 |
| 6,054,472 A | 4/2000 | Armistead et al. | 514/374 |

FOREIGN PATENT DOCUMENTS

| | | |
|---|---|---|
| DE | 2221866 A | 12/1972 |
| GB | 1171904 A | 11/1969 |
| GB | 1395641 * | 5/1975 |
| WO | WO 94/01105 | 1/1994 |
| WO | WO 94/12184 | 6/1994 |

OTHER PUBLICATIONS

Advani et al., Chemical Abstracts, 70:3898, 1969.*
Brooker et al., Chemical Abstracts, 78:85934, 1973.*
Pande et al., Chemical Abstracts, 99:139834, 1983.*
Ishikawa et al., Chemical Abstracts, 104:202306, 1986.*
C.R. Gregory et al., "Treatment With Rapamycin and Mycophenolic Acid Reduces Arterial Intimal Thickening Produced by Mechanical Injury and Allows Endothelial Replacement", *Transplatation*, 59(5), pp. 655–661 (1995).
J.A. Huete–Perez et al., "Identification of the IMP Binding Site in the IMP Dehydrogenase from *Tritrichomonas foetus*", *Biochemistry*, 34, pp. 13889–13894 (1995).
G.M. Makara et al. "Nuclear Magnetic Resonance and Molecular Modeling Study on Mycophenolic Acid: Implications for Binding to Inosine Monophosphate Dehydrogenase", *J. Med. Chem.* 39, pp. 1236–1242 (1996).
F. Merchan et al., "Synthesis of 2–Aryliminoimidazolidines and 2–Arylaminobenzimidazoles from Methyl N–Aryldithiocarbamates," *Synthesis*, vol. 6, pp. 482–484 (1982).
C. Montero et al., "Demonstration of Induction of Erythrocyte Inosine Monophosphate Dehydrogenase Activity in Ribavirin–Treated Patients Using a High Performance Liquid Chromatography Linked Method", *Clinica Chimica Acta*, 238, pp. 169–178 (1995).
R.E. Morris, "New Small Molecule Immunosuppressants for Transplantation: Review of Essential Concepts", *The Journal of Heart and Lung Transplantation*, 12, pp. S275–S286 (1993).
F.G. Whitby et al., "Preliminary X–Ray Crystallographic Analysis of *Tritrichomonas foetus* Inosine–5'–Monophosphate Dehydrogenase", *Proteins: Structure, Function and Genetics*, 23, pp. 598–603 (1995).

* cited by examiner

*Primary Examiner*—Richard L. Raymond
(74) *Attorney, Agent, or Firm*—Fish & Neave; James F. Haley, Jr.; Larry Coury

(57) ABSTRACT

The present invention relates to a novel class of compounds which are IMPDH inhibitors. This invention also relates to pharmaceutical compositions comprising these compounds. The compounds and pharmaceutical compositions of this invention are particularly well suited for inhibiting IMPDH enzyme activity and consequently, may be advantageously used as therapeutic agents for IMPDH mediated processes. This invention also relates to methods for inhibiting the activity of IMPDH using the compounds of this invention and related compounds.

12 Claims, No Drawings

INHIBITORS OF IMPDH ENZYME

CROSS REFERENCE TO RELATED APPLICATIONS

This is a continuation-in-part of copending international application Ser. No. PCT/US98/04932, filed Mar. 13, 1998, which claims the benefit of the filing date of United States provisional application Ser. No. 60/042,443, filed Mar. 28, 1997, which is a continuation-in-part of United States application Ser. No. 08/816,764, filed Mar. 14, 1997, now U.S. Pat. No. 5,932,600, issued Aug. 3, 1999.

TECHNICAL FIELD OF THE INVENTION

The present invention relates to a novel class of compounds which inhibit IMPDH. This invention also relates to pharmaceutical compositions comprising these compounds. The compounds and pharmaceutical compositions of this invention are particularly well suited for inhibiting IMPDH enzyme activity and consequently, may be advantageously used as therapeutic agents for IMPDH mediated processes. This invention also relates to methods for inhibiting the activity of IMPDH using the compounds of this invention and related compounds.

BACKGROUND OF THE INVENTION

The synthesis of nucleotides in organisms is required for the cells in those organisms to divide and replicate. Nucleotide synthesis in mammals may be achieved through one of two pathways: the de novo synthesis pathway or the salvage pathway. Different cell types use these pathways to a different extent.

Inosine-5'-monophosphate dehydrogenase (IMPDH; EC 1.1.1.205) is an enzyme involved in the de novo synthesis of guanosine nucleotides. IMPDH catalyzes the NAD-dependent oxidation of inosine-5'-monophosphate (IMP) to xanthosine-5'-monophosphate (XMP) [Jackson R. C. et. al., Nature, 256, pp. 331–333, (1975)].

IMPDH is ubiquitous in eukaryotes, bacteria and protozoa [Y. Natsumeda & S. F. Carr, Ann. N.Y. Acad., 696, pp. 88–93 (1993)]. The prokaryotic forms share 30–40% sequence identity with the human enzyme. Regardless of species, the enzyme follows an ordered Bi-Bi reaction sequence of substrate and cofactor binding and product release. First, IMP binds to IMPDH. This is followed by the binding of the cofactor NAD. The reduced cofactor, NADH, is then released from the complex, followed by the product, XMP [S. F. Carr et al., J. Biol. Chem., 268, pp. 27286–90 (1993); E. W. Holmes et al., Biochim. Biophys. Acta, 364, pp. 209–217 (1974)]. This mechanism differs from that of most other known NAD-dependent dehydrogenases, which have either a random order of substrate addition or require NAD to bind before the substrate.

Two isoforms of human IMPDH, designated type I and type II, have been identified and sequenced [F. R. Collart and E. Huberman, J. Biol. Chem., 263, pp. 15769–15772, (1988); Y. Natsumeda et. al., J. Biol. Chem., 265, pp. 5292–5295, (1990)]. Each is 514 amino acids, and they share 84% sequence identity. Both IMPDH type I and type II form active tetramers in solution, with subunit molecular weights of 56 kDa [Y. Yamada et. al., Biochemistry, 27, pp. 2737–2745 (1988)].

The de novo synthesis of guanosine nucleotides, and thus the activity of IMPDH, is particularly important in B and T-lymphocytes. These cells depend on the de novo, rather than salvage pathway to generate sufficient levels of nucleotides necessary to initiate a proliferative response to mitogen or antigen [A. C. Allison et. al., Lancet II, 1179, (1975) and A. C. Allison et. al., Ciba Found. Symp., 48, 207, (1977)]. Thus, IMPDH is an attractive target for selectively inhibiting the immune system without also inhibiting the proliferation of other cells.

Immunosuppression has been achieved by inhibiting a variety of enzymes including for example, the phosphatase calcineurin (inhibited by cyclosporin and FK-506); dihydroorotate dehydrogenase, an enzyme involved in the biosynthesis of pyrimidines (inhibited by leflunomide and brequinar); the kinase FRAP (inhibited by rapamycin); and the heat shock protein hsp70 (inhibited by deoxyspergualin). [See B. D. Kahan, Immunological Reviews, 136, pp. 29–49 (1993); R. E. Morris, The Journal of Heart and Lung Transplantation, 12(6), pp. S275–S286 (1993)].

Inhibitors of IMPDH are also known. U.S. Pat. Nos. 5,380,879 and 5,444,072 and PCT publications WO 94/01105 and WO 94/12184 describe mycophenolic acid (MPA) and some of its derivatives as potent, uncompetitive, reversible inhibitors of human IMPDH type I ($K_i$=33 nM) and type II ($K_i$=9 nM). MPA has been demonstrated to block the response of B and T-cells to mitogen or antigen [A. C. Allison et. al., Ann. N. Y. Acad. Sci., 696, 63, (1993).

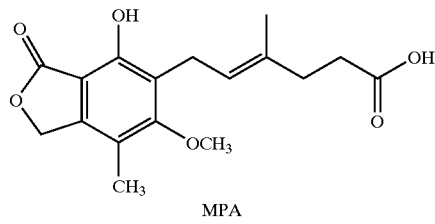

MPA

Immunosuppressants, such as MPA, are useful drugs in the treatment of transplant rejection and autoimmune diseases. [R. E. Morris, Kidney Intl., 49, Suppl. 53, S-26, (1996)]. However, MPA is characterized by undesirable pharmacological properties, such as gastrointestinal toxicity and poor bioavailability. [L. M. Shaw, et. al., Therapeutic Drug Monitoring, 17, pp. 690–699, (1995)].

Nucleoside analogs such as tiazofurin, ribavirin and mizoribine also inhibit IMPDH [L. Hedstrom, et. al. Biochemistry, 29, pp. 849–854 (1990)]. These compounds, which are competitive inhibitors of IMPDH, suffer from lack of specificity to this enzyme.

Mycophenolate mofetil, a prodrug which quickly liberates free MPA in vivo, was recently approved to prevent acute renal allograft rejection following kidney transplantation. [L. M. Shaw, et. al., Therapeutic Drug Monitoring, 17, pp. 690–699, (1995); H. W. Sollinger, Transplantation, 60, pp. 225–232 (1995)]. Several clinical observations, however, limit the therapeutic potential of this drug. [L. M. Shaw, et. al., Therapeutic Drug Monitoring, 17, pp. 690–699, (1995)]. MPA is rapidly metabolized to the inactive glucuronide in vivo. [A. C., Allison and E. M. Eugui, Immunological Reviews, 136, pp. 5–28 (1993)]. The glucuronide then undergoes enterohepatic recycling causing accumulation of MPA in the gastrointestinal tract where it cannot exert its IMPDH inhibitory activity on the immune system. This effectively lowers the drug's in vivo potency, while increasing its undesirable gastrointestinal side effects.

It is also known that IMPDH plays a role in other metabolic events. Increased IMPDH activity has been observed in rapidly proliferating human leukemic cell lines and other tumor cell lines, indicating IMPDH as a target for anticancer as well as immunosuppressive chemotherapy [M. Nagai et. al., *Cancer Res.*, 51, pp. 3886–3890, (1991)]. IMPDH has also been shown to play a role in the proliferation of smooth muscle cells, indicating that inhibitors of IMPDH, such as MPA or rapamycin, may be useful in preventing restenosis or other hyperproliferative vascular diseases [C. R. Gregory et al., *Transplantation*, 59, pp. 655–61 (1995); PCT publication WO 94/12184; and PCT publication WO 94/01105].

Additionally, IMPDH has been shown to play a role in viral replication in some viral cell lines. [S. F. Carr, *J. Biol. Chem.*, 268, pp. 27286–27290 (1993)]. Analogous to lymphocyte and tumor cell lines, the implication is that the de novo, rather than the salvage, pathway is critical in the process of viral replication.

The IMPDH inhibitor ribavirin is currently being evaluated for the treatment of hepatitis C virus (HCV) and hepatitis B virus (HBV) infection and disease. Ribavirin enhances the sustained efficacy of interferon in HBV and HCV treatment. However, the therapeutic potential of ribavirin is limited by its lack of a sustained response in monotherapy and broad cellular toxicity.

Thus, there remains a need for potent IMPDH inhibitors with improved pharmacological properties. Such inhibitors would have therapeutic potential as immunosuppressants, anticancer agents, antivascular hyperproliferative agents, antiinflammatory agents, antifungal agents, antipsoriatic and antiviral agents.

SUMMARY OF THE INVENTION

The present invention provides compounds, and pharmaceutically acceptable derivatives thereof, that are useful as inhibitors of IMPDH. These compounds can be used alone or in combination with other therapeutic or prophylactic agents, such as antivirals, antiinflammatory agents, antibiotics, and immunosuppressants for the treatment or prophylaxis of transplant rejection and autoimmune disease. Additionally, these compounds are useful, alone or in combination with other agents, as therapeutic and prophylactic agents for antiviral, antitumor, anticancer, antiinflammatory, antifungal, antipsoriatic, immunosuppressive, and restenosis therapy regimens.

The invention also provides pharmaceutical compositions comprising the compounds of this invention, as well as multi-component compositions comprising additional IMPDH compounds together with an immunosuppressant. The invention also provides methods of using the compounds of this invention, as well as other related compounds, for the inhibition of IMPDH.

The compounds of this invention, as well as those used in the methods of this invention demonstrate a different metabolic profile than MPA and its derivatives. Because of this difference, methods of this invention and the compounds used therein may offer advantages as therapeutics for IMPDH mediated disease. These advantages include increased overall therapeutic benefit and reduction in deleterious side effects.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Ac | acetyl |
| Me | methyl |
| Et | ethyl |
| Bn | benzyl |
| CDI | carbonyldiimidazole |
| DIEA | diisopropylethylamine |
| DMAP | dimethylaminopyridine |
| DMF | dimethylformamide |
| DMSO | dimethylsulfoxide |
| EDC | 1-(3-dimethylaminopropyl)-3-ethylcarbodiimide hydrochloride |
| EtOAc | ethyl acetate |
| THF | tetrahydrofuran |

The following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

The terms "halo" or "halogen" refer to a radical of fluorine, chlorine, bromine or iodine.

The term "immunosuppressant" refers to a compound or drug which possesses immune response inhibitory activity. Examples of such agents include cyclosporin A, FK506, rapamycin, leflunomide, deoxyspergualin, prednisone, azathioprine, mycophenolate mofetil, OKT3, ATAG, interferon and mizoribine.

The term "interferon" refers to all forms of interferons, including but not limited to alpha, beta and gamma forms.

IMPDH-mediated disease refers to any disease state in which the IMPDH enzyme plays a regulatory role in the metabolic pathway of that disease. Examples of IMPDH-mediated disease include transplant rejection and autoimmune diseases, such as rheumatoid arthritis, multiple sclerosis, juvenile diabetes, asthma, and inflammatory bowel disease, as well as inflammatory diseases, cancer, viral replication diseases, and vascular diseases.

For example, the compounds, compositions and methods of using them of this invention may be used in the treatment of transplant rejection (e.g., kidney, liver, heart, lung, pancreas (islet cells), bone marrow, cornea, small bowel and skin allografts and heart valve xenografts) and autoimmune diseases, such as rheumatoid arthritis, multiple sclerosis, juvenile diabetes, asthma, inflammatory bowel disease (Crohn's disease, ulcerative colitus), lupus, diabetes, mellitus myasthenia gravis, psoriasis, dermatitis, eczema, seborrhea, pulmonary inflammation, eye uveitis, hepatitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, and glomerulonephritis, scleroderma, lichen planus, viteligo (depigmentation of the skin), autoimmune thyroiditis, and alveolitis, inflammatory diseases such as osteoarthritis, acute pancreatitis, chronic pancreatitis, asthma and adult respiratory distress syndrome, as well as in the treatment of cancer and tumors, such as solid tumors, lymphomas and leukemia, vascular diseases, such as restenosis, stenosis and artherosclerosis, and viral DNA and RNA replication diseases.

Additionally, IMPDH enzymes are also known to be present in bacteria and thus may regulate bacterial growth. As such, the IMPDH-inhibitor compounds, compositions and methods described herein may be useful in treatment or prevention of bacterial infection, alone or in combination with other antibiotic agents.

The term "treating" as used herein refers to the alleviation of symptoms of a particular disorder in a patient or the improvement of an ascertainable measurement associated with a particular disorder. As used herein, the term "patient" refers to a mammal, including a human.

The terms "HBV", "HCV" and "HGV" refer to hepatitis-B, hepatitis-C and hepatitis-G virus, respectively.

According to one embodiment, the invention provides methods of inhibiting IMPDH activity in a mammal comprising the step of administering to said mammal, a compound of formula I:

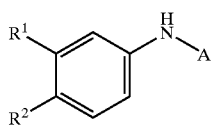

I wherein:
A is a saturated, unsaturated or partially saturated monocyclic or bicyclic ring system optionally comprising up to 4 heteroatoms selected from N, O, and S wherein each A optionally comprises up to 4 substituents selected from $R^1$, $R^4$ and $R^5$;

each $R^1$ is hydrogen halogen, CN, $NO_2$, $CF_3$, $OCF_3$, OH, $R^3$, $OR^3$, 1,2-methylenedioxy, 1,2-ethylenedioxy, $SR^3$, $S(O)R^3$, $SO_2R^3$, $NH_2$, $NHR^3$, $N(R^3)_2$, $NR^3R^9$, COOH, or $COOR^3$;

each $R^2$ is independently $R^1$ or a monocyclic ring system consisting of 5 to 6 members per ring, wherein said ring system optionally comprises up to 4 heteroatoms selected from N, O, and S, and wherein a $CH_2$ adjacent to said N, O or S maybe substituted with C(O); and each $R^2$ optionally comprises up to 2 substituents, each substituent independently selected from $R^1$;

each $R^3$ is independently $(C_1-C_4)$-straight or ranched alkyl, or $(C_2-C_4)$-straight or branched alkenyl or alkynyl;

each $R^4$ is independently $(C_1-C_6)$-straight or branched alkyl, or $(C_2-C_6)$-straight or branched alkenyl or alkynyl; and each $R^4$ optionally comprises up to 2 substituents, wherein:
the first of said substituents, if present, is $R^1$, $R^5$ or $R^8$, and
the second of said substituents, if present, is $R^1$;

each $R^5$ is independently selected from $OR^6$, $OC(O)R^7$, $OC(O)R^6$, $OC(O)OR^7$, $OC(O)OR^6$, $OC(O)N(R^7)_2$, $OP(O)(OR^7)_2$, $SR^7$, $SR^6$, $S(O)R^7$, $S(O)R^6$, $SO_2R^7$, $SO_2R^6$, $SO_2N(R^7)_2$, $SO_2NR^6R^7$, $SO_3R^7$, $C(O)R^6$, $C(O)OR^6$, $C(O)R^7$, $C(O)OR^7$, $NC(O)C(O)R^7$, $NC(O)C(O)R^6$, $NC(O)C(O)OR^7$, $NC(O)C(O)N(R^7)_2$, $C(O)N(R^7)_2$, $C(O)N(OR^7)R^7$, $C(O)N(OR^7)R^6$, $C(NOR^7)R^7$, $C(NOR^7)R^6$, $N(R^7)_2$, $NR^7C(O)R^6$, $NR^7C(O)R^7$, $NR^6C(O)R^6$, $NR^7C(O)OR^7$, $NR^7C(O)OR^6$, $NR^7C(O)N(R^7)_2$, $NR^7C(O)NR^6R^7$, $NR^7SO_2R^7$, $NR^7SO_2R^6$, $NR^7SO_2N(R^7)_2$, $NR^7SO_2NR^6R^7$, $N(OR^7)R^7$, $N(OR^7)R^6$, P(O)(OR^7)N(R^7)_2$, $P(O)(OR^7)_2$, $P(O)(N(R^7)_2)_2$, and $P(O)(OR^7)R^7$.

$R^6$ is a monocyclic or a bicyclic ring system consisting of 5 to 6 members per ring, wherein said ring system optionally comprises up to 4 heteroatoms selected from N, O, and S, and wherein a $CH_2$ adjacent to any of said N, O, or S heteroatoms is optionally substituted with C(O); and each $R^6$ optionally comprises up to 3 substituents, each substituent independently selected from $R^1$;

each $R^7$ is independently H, $(C_1-C_4)$-straight or branched alkyl, or $(C_2-C_4)$ straight or branched alkenyl; and each $R^7$ optionally comprises a substituent that is $R^8$;

$R^8$ is a monocyclic or a bicyclic ring system consisting of 5 to 6 members per ring, wherein said ring system optionally comprises up to 4 heteroatoms selected from N, O, and S, and wherein a $CH_2$ adjacent to said N, O or S maybe substituted with C(O); and each $R^8$ optionally comprises up to 2 substituents independently chosen from H, $(C_1-C_4)$-straight or branched alkyl, $(C_2-C_4)$ straight or branched alkenyl, 1,2-methylenedioxy, 1,2-ethylenedioxy and $(CH_2)_n-R^1$;
wherein n is 0, 1 or 2;

$R^9$ is an amino protecting group; and
wherein any carbon atom in any $R^3$, $R^4$ or $R^7$ is optionally replaced by O, S, SO, $SO_2$, NH, or $N(C_1-C_4)$-alkyl.

The term "substituted" refers to the replacement of one or more hydrogen radicals in a given structure with a radical selected from a specified group. When more than one hydrogen radical may be replaced with a substituent selected from the same specified group, the substituents may be either the same or different at every position.

The term "monocyclic or bicyclic ring system consisting of 5 to 6 members per ring" refers to 5 or 6 member monocyclic rings and 8, 9 and 10 membered bicyclic ring structures, wherein each bond in each ring may possess any degree of saturation that is chemically feasible. When such structures contain substituents, those substituents may be at any position of the ring system, unless otherwise specified.

As specified, such ring systems may optionally comprise up to 4 heteroatoms selected from N, O or S. Those heteroatoms may replace any carbon atoms in these ring systems as long as the resulting compound is chemically stable.

The term "amino protecting group" refers to a suitable chemical group which may be attached to a nitrogen atom. The term "protected" refers to when the designated functional group is attached to a suitable chemical group (protecting group). Examples of suitable amino protecting groups and protecting groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

Preferably, in methods employing the compounds of formula I, each A optionally comprises up to 4 substituents selected from $R^1$, $R^4$ and $R^5$, preferably wherein at least one substituent, if present, is selected from $R^4$ and $R^5$; also preferably wherein A comprises up to 4 substituents, each independently selected from $R^1$; and also preferably wherein A comprises up to 4 substituents, one substituent, if present, is selected from $R^4$ and $R^5$ and the remaining substituents, if present, are independently selected from $R^1$.

More preferably, in methods employing the compounds of formula I, A is a monocyclic aromatic ring system optionally comprising up to 4 heteroatom selected from N, O, and S wherein each A optionally comprises up to 4 substituents selected from $R^1$, $R^4$ and $R^5$, preferably wherein at least one substituent, if present, is selected from $R^4$ and $R^5$; also preferably wherein A comprises up to 4 substituents, each independently selected from $R^1$; and also preferably wherein A comprises up to 4 substituents, one substituent, if present, is selected from $R^4$ and $R^5$ and the remaining substituents, if present, are independently selected from $R^1$.

Also more preferably, in methods employing the compounds of formula I, A is a bicyclic aromatic ring system optionally comprising up to 4 heteroatoms selected from N, O, and S, wherein each A optionally comprises up to 4 substituents selected from $R^1$, $R^4$ and $R^5$, preferably wherein at least one substituent, if present, is selected from $R^4$ and $R^5$; also preferably wherein A comprises up to 4 substituents, each independently selected from $R^1$; and also preferably wherein A comprises up to 4 substituents, one substituent, if present, is selected from $R^4$ and $R^5$ and the remaining substituents, if present, are independently selected from $R^1$.

More preferably, in methods employing the compounds of formula I, are those methods wherein the compound has the structure of the formula:

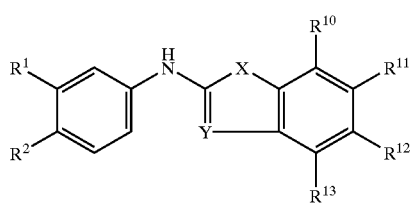

II wherein:

$R^{10}$, $R^{11}$, $R^{12}$ and $R^{13}$ are each independently selected from $R^1$ and $R^4$, wherein only one of $R^{10}$, $R^{11}$, $R^{12}$ and $R^{13}$ may simultaneously be $R^4$; and X and Y are independently selected from $CH_2$, $CHR^3$, $CHR^4$, O, S, NH, $NR^3$, $NR^4$, CH, $CR^3$, $CR^4$, and N.

The present invention also provides compounds which are useful in inhibiting IMPDH. According to one embodiment, the compounds have the structure and definitions of formula I above. Preferably, the invention provides compounds with the structure and definitions of formula II above.

More preferably, the invention provides a compound of formula III:

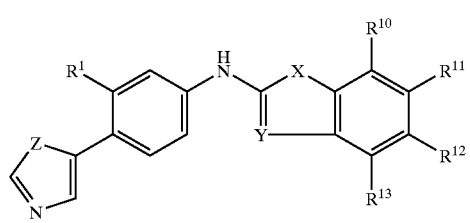

III wherein $R^1$, $R^{10}$, $R^{11}$, $R^{12}$, $R^{13}$, X and Y are as defined in formula II and Z is O, S, NH or $NR^3$, wherein $R^3$ is as defined in formula I.

According to an alternate embodiment, the invention provides a compound of the formula IV:

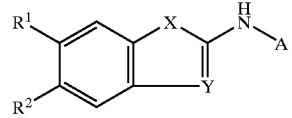

IV wherein $R^1$, $R^2$, A, X and Y are as defined for formula II.

Table I lists preferred individual compounds of the invention and preferred compounds employed in the compositions and methods of this invention.

TABLE I

1 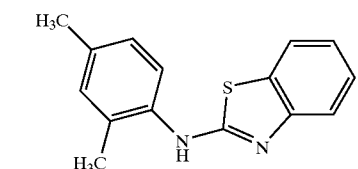

2 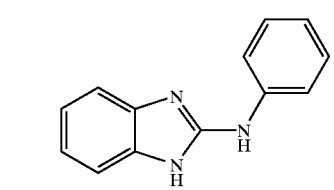

3 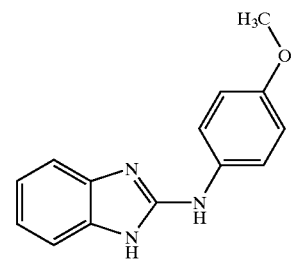

4 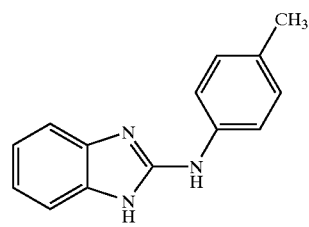

5 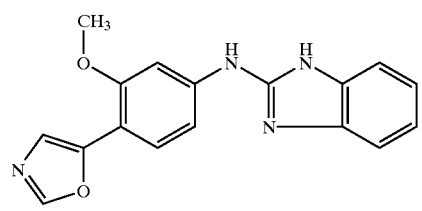

6 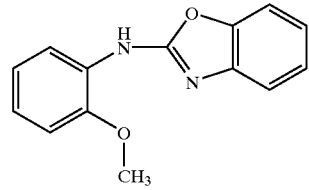

TABLE I-continued
7
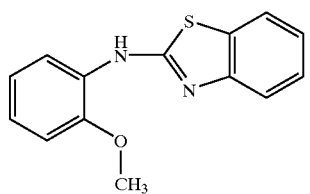
8
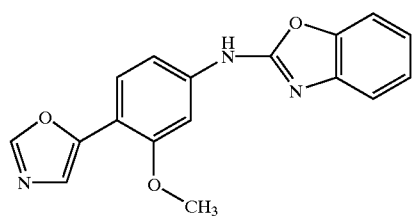
9
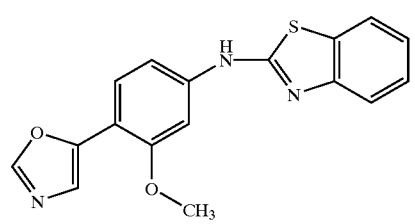
10
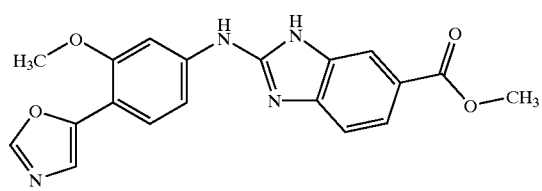
11
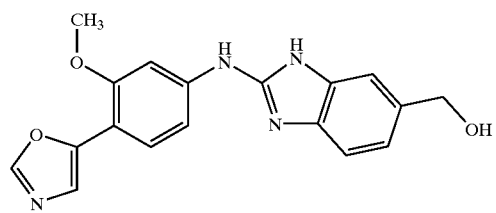
12
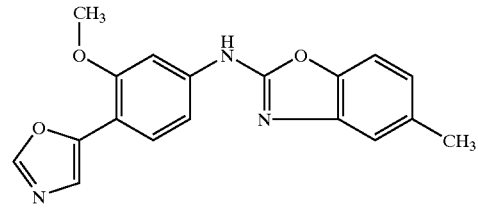
13
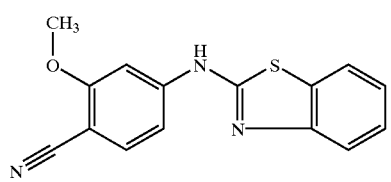
TABLE I-continued
14
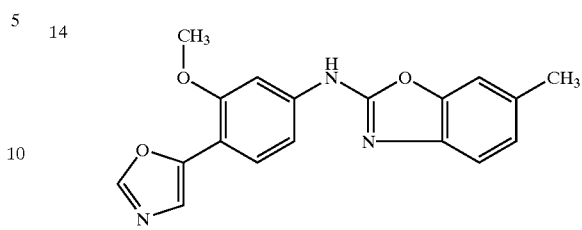
15
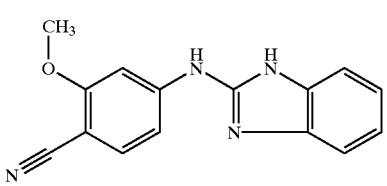
16
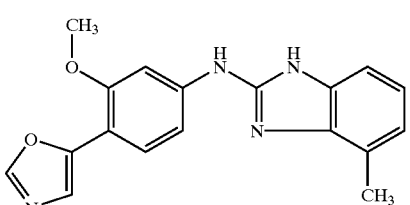
17
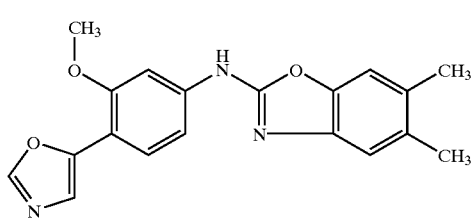
18
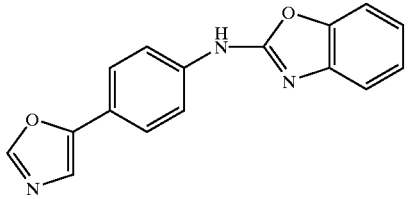
19
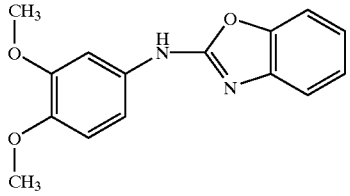
20
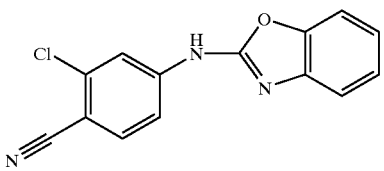

TABLE I-continued

21. [structure: 2-methoxy-4-cyano-phenyl linked via NH to benzoxazole]

22. [structure: 2-methoxy-4-(oxazol-5-yl)phenyl linked via NH to 5-methylbenzoxazole]

23. [structure: 2-chloro-4-(oxazol-5-yl)phenyl linked via NH to benzoxazole]

24. [structure: 3-methoxyphenyl linked via NH to benzoxazole]

25. [structure: 2-methoxy-4-(oxazol-5-yl)phenyl linked via NH to 7-allyl-benzoxazole]

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

As used herein, the compounds of this invention, including the compounds of formulae I-IV, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae I-IV.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium, potassium), alkaline earth metal (e.g., magnesium), ammonium and N—$(C_{1-4}$ alkyl$)_4^+$ salts.

This invention also envisions the quaternization of any basic nitrogen-containing groups of the compounds disclosed herein. Water or oil-soluble or dispersible products may be obtained by such quaternization.

The compounds of this invention may be synthesized using conventional techniques. Advantageously, these compounds are conveniently synthesized from readily available starting materials.

In general, compounds of formula I-IV are conveniently obtained via methods illustrated in General Synthetic Schemes 1–2.

In General Synthetic Scheme 1 (see below), an A, B, C, D-substituted aniline is reacted with an $R^{10}$, $R^{11}$, $R^{12}$, $R^{13}$-substituted halo-substituted heterocycle under standard conditions to give the desired amine. In this process, A, B, C, D and $R^{10}$, $R^{11}$, $R^{12}$, $R^{13}$ may be one or more independent substituents (or their suitably protected variants) as exemplified by the ring substituents listed for compounds of formulae I-IV above, at any position on the aromatic ring. Additionally, the halo leaving group may alternatively be any suitable equivalent, for example, mesylate or tosylate.

Scheme 1

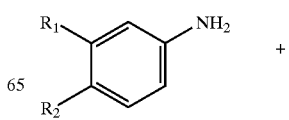
+

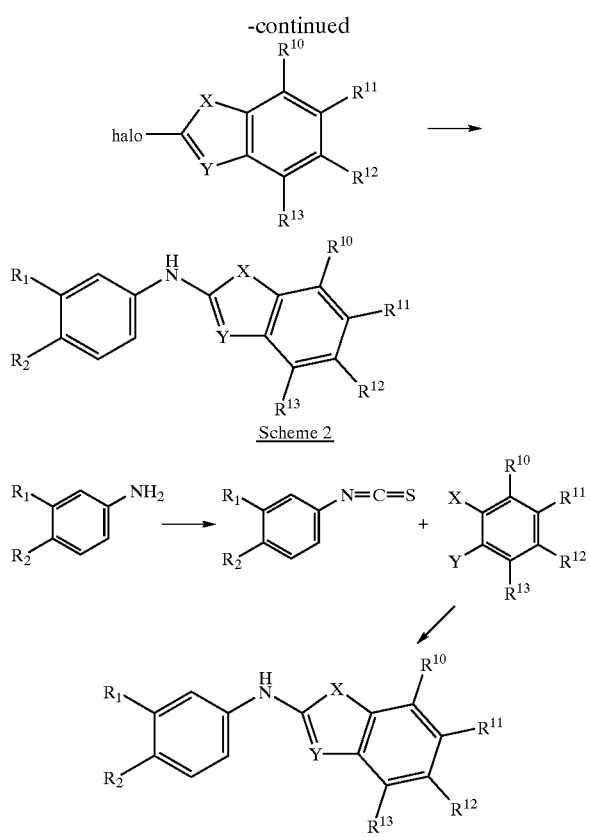

Scheme 2

An alternate synthetic route is illustrated in General Synthetic Scheme 2 (see above). An $R^1$, $R^2$-substituted aniline is converted to the corresponding thioisocyanate under standard conditions. This product is then treated with an aniline, where $R^{10}$, $R^{11}$, $R^{12}$, $R^{13}$ may be one or more independent substituents (or their suitably protected variants) as exemplified by the ring substituents listed for compounds of formulae I-IV above, at any position on the aromatic ring and X and Y are as exemplified in the compounds of formulae I-IV, to give the desired substituted amine products.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are ligands for IMPDH. Accordingly, these compounds are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). [See C. Montero et al., *Clinica Chimica Acta*, 238, pp. 169–178 (1995)].

Pharmaceutical compositions of this invention comprise a compound of formula I or IV or a pharmaceutically acceptable salt thereof; an additional agent selected from an immunosuppressant, an anticancer agent, an antiviral agent, antiinflammatory agent, antifungal agent, antibiotic, or an antivascular hyperproliferation compound; and any pharmaceutically acceptable carrier, adjuvant or vehicle. Alternate compositions of this invention comprise a compound of formulae I-IV or a pharmaceutically acceptable salt thereof; and a pharmaceutically acceptable carrier, adjuvant or vehicle. Such composition may optionally comprise an additional agent selected from an immunosuppressant, an anticancer agent, an antiviral agent, antiinflammatory agent, antifungal agent, antibiotic, or an antivascular hyperproliferation compound.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of formulae I-IV.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica, *Ph. Helv.,* or a similar alcohol, or carboxymethyl celluose or similar dispersing agents which are commonly used in the formulation of pharmaceutically acceptable dosage forms such as emulsions and or suspensions Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the IMPDH inhibitory compounds described herein are useful in a monotherapy and/or in combination therapy for the prevention and treatment of IMPDH mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of an IMPDH inhibitor of formulae I-IV and one or more additional therapeutic or prophylactic agents, both the IMPDH inhibitor and the additional agent should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, interferon and mizoribine.

According to an alternate embodiment, the pharmaceutical compositions of this invention may additionally comprise an anticancer agent. Examples of anticancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines, interferon and thioxantheres.

According to another alternate embodiment, the pharmaceutical compositions of this invention may additionally comprise an antiviral agent. Examples of antiviral agents include, but are not limited to, Cytovene, Ganciclovir, trisodium phosphonoformate, Ribavirin, d4T, ddI, AZT, and acyclovir.

According to yet another alternate embodiment, the pharmaceutical compositions of this invention may additionally comprise an antivascular hyperproliferative agent. Examples of antivascular hyperproliferative agents include, but are not limited to, HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin and 5-(3'-pyridinylmethyl)benzofuran-2-carboxylate.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In an alternate embodiment, this invention provides methods of treating or preventing IMPDH mediated disease in a mammal comprising the step of administrating to said mammal any of the pharmaceutical compositions and combinations described above. If the pharmaceutical composition only comprises the IMPDH inhibitor of this invention as the active component, such methods may additionally comprise the step of administering to said mammal an agent selected from an antiinflammatory agent, immunosuppressant, an anticancer agent, an antiviral agent, or an antivascular hyperproliferation compound. Such additional agent may be administered to the mammal prior to, concurrently with, or following the administration of the IMPDH inhibitor composition.

In a preferred embodiment, these methods are useful in suppressing an immune response in a mammal. Such methods are useful in treating or preventing diseases, including, transplant rejection (e.g., kidney, liver, heart, lung, pancreas (islet cells), bone marrow, cornea, small bowel and skin allografts and heart valve xenografts), graft versus host disease, and autoimmune diseases, such as rheumatoid arthritis, multiple sclerosis, juvenile diabetes, asthma, inflammatory bowel disease (Crohn's disease, ulcerative colitis), lupus, diabetes, mellitus myasthenia gravis, psoriasis, dermatitis, eczema, seborrhoea, pulmonary inflammation, eye uveitis, hepatitis, Gravels disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, viteligo (depigmentation of the skin), autoimmune thyroiditis, and alveolitis.

These methods comprise the step of administering to the mammal a composition comprising a compound of any of formulae I-IV and a pharmaceutically acceptable adjuvant. In a preferred embodiment, this particular method comprises the additional step of administering to said mammal a composition comprising an additional immunosuppressant and a pharmaceutically acceptable adjuvant.

Alternatively, this method comprises the step of administering to said mammal a composition comprising a compound of formulae I-IV; an additional immunosuppressive agent and a pharmaceutically acceptable adjuvant.

In an alternate preferred embodiment, these methods are useful for inhibiting viral replication in a mammal. Such methods are useful in treating or preventing DNA and RNA viral diseases caused by, for example, HTLV-1 and HTLV-2, HIV-1 and HIV-2, nasopharyngeal carcinoma virus, yellow fever, dengue fever, HBV, HCV, HGV, yellow fever virus, dengue fever virus, Japanese encephalitis virus, human papilloma virus, rhinoviruses and Herpes viruses, such as Epstein-Barr, cytomegaloviruses, Herpes Simplex, Types 1 and 2, or Type 6. [See, U.S. Pat. No. 5,380,879].

These methods comprise the step of administering to the mammal a composition comprising a compound of any of formulae I-IV, and a pharmaceutically acceptable adjuvant. In a preferred embodiment, this particular method comprises the additional step of administering to said mammal a composition comprising an additional antiviral agent and a pharmaceutically acceptable adjuvant.

Alternatively, this method comprises the step of administering to said mammal a composition comprising a compound of formulae I-IV; an additional antiviral agent and a pharmaceutically acceptable adjuvant.

In another alternate preferred embodiment, these methods are useful for inhibiting vascular cellular hyperproliferation in a mammal. Such methods are useful in treating or preventing diseases, including, restenosis, stenosis, artherosclerosis and other hyperproliferative vascular disease.

These methods comprise the step of administering to the mammal a composition comprising a compound of any of formulae I-IV, and a pharmaceutically acceptable adjuvant. In a preferred embodiment, this particular method comprises the additional step of administering to said mammal a composition comprising an additional antivascular hyperproliferative agent and a pharmaceutically acceptable adjuvant.

Alternatively, this method comprises the step of administering to said mammal a composition comprising a compound of formulae I-IV; an additional antivascular hyperproliferative agent and a pharmaceutically acceptable adjuvant.

In another alternate preferred embodiment, these methods are useful for inhibiting tumors and cancer in a mammal. Such methods are useful in treating or preventing diseases, including, tumors and malignancies, such as lymphoma, leukemia and other forms of cancer.

These methods comprise the step of administering to the mammal a composition comprising a compound of any of formulae I-IV, and a pharmaceutically acceptable adjuvant. In a preferred embodiment, this particular method comprises the additional step of administering to said mammal a composition comprising an additional antitumor or anticancer agent and a pharmaceutically acceptable adjuvant.

Alternatively, this method comprises the step of administering to said mammal a composition comprising a compound of formulae I-IV; an additional antitumor or anticancer agent and a pharmaceutically acceptable adjuvant.

In another alternate preferred embodiment, these methods are useful for inhibiting inflammation and inflammatory diseases in a mammal. Such methods are useful in treating or preventing diseases, including, osteoarthritis, acute pancreatitis, chronic pancreatitis, asthma and adult respiratory distress syndrome.

These methods comprise the step of administering to the mammal a composition comprising a compound of any of formulae I-IV, and a pharmaceutically acceptable adjuvant. In a preferred embodiment, this particular method comprises the additional step of administering to said mammal a composition comprising an antiinflammatory agent and a pharmaceutically acceptable adjuvant.

In order that this invention be more fully understood, the following examples are set forth. These examples are for the purpose of illustration only and are not to be construed as limiting the scope of the invention in any way.

General Materials and Methods

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Analytical HPLC was carried out using a Rainin Mycrosorb-MV, 5μ Cyano reverse phase column, 3.9 mm×150 mm, with a flow rate of 1.0 mL/minute and a solvent gradient of 5–100% acetonitrile (0.1% TFA) in water (0.1% TFA). HPLC retention times were recorded in minutes. NMR spectral data was acquired using a Bruker AMX500 in the indicated solvent.

The IMP dehydrogenase HPLC assay follows our standard conditions for the enzymatic production of XMP and NADH from IMP and NAD, but utilizes high pressure liquid chromatography on a C18 column with ion pairing reagents to separate all four components. The extent of reaction is then determined from the resulting product peak areas. This assay is particularly useful for determining the inhibition profiles of compounds which have significant absorbance in the UV-visible region between 290 and 340 nM.

The reaction mixture typically contains 0.1 M KPi; pH 8.0, 0.1M KCl, 0.5 mM EDTA, 2 mM DTT, and 0.2 mM each of IMP and NAD. This solution is incubated at 37° C. for 10 minutes. The reaction is started by the addition of enzyme to a final concentration of 20 to 100 nM, and is allowed to proceed for 10 minutes. After the allotted time, the reaction is quenched by the addition of mycophenolic acid to a final concentration of 0.01 mM.

The extent of conversion is monitored by HPLC using a Rainin Microsorb ODS column C18-200 of dimensions 4.6×10 mm and a solvent system containing tetrabutylammonium sulfate (5mM) in 0.1 M KPi pH 6.0 with a 0–30% methanol gradient over 15 minutes. A similar solvent system has been used previously for the purification of halo-IMP derivatives. [L. C. Antionio and J. C. Wu, *Biochemistry*, 33, 1753–1759 (1994).] A UV-monitor set at 254 nM is used to detect the four components, and the product peaks are integrated to determine the extent of conversion of the substrates.

For the analysis of inhibitors, the compound in question is dissolved in DMSO to a final concentration of 20 mM and added to the initial assay mixture at the desired concentration in a volume of 2–5% (v/v). The reaction is started by the addition of enzyme and after 10 minutes is quenched as above. After HPLC analysis, the product areas are used to determine the extent of conversion relative to a control assay containing only DMSO and no test compound. IC50 or Ki values are determined from non linear least squares fitting of conversion vs concentration curves to the tight-binding equations of Henderson. [P. J. F. Henderson, *Biochem. J.*, 127, 321 (1972).]

We have measured the inhibition constants of each compound against IMPDH using an adaptation of the method first reported by Magasanik. [B. Magasanik, H. S. Moyed, and L. B. Gehring *J. Biol. Chem.*, 226, p.339 (1957)].

Insofar as compounds of formulae I-IV are able to inhibit IMPDH, they are of evident clinical utility for the treatment of IMPDH mediated disease. These tests are predictive of the compounds ability to inhibit IMPDH in vivo.

Experimental Section

Synthesis of Representative Examples:

EXAMPLE 1

Synthesis of Compound 5

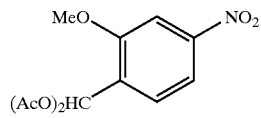

To a solution of glacial acetic acid (95 mL), acetic anhydride (95 mL, 1 mole) and 2-methoxy-4-nitrotoluene (10 g, 50 mmole) at 0° C. was added conc. $H_2SO_4$ (14.2 mL) in a dropwise fashion. Upon complete addition, $CrO_3$ (16.67 g, 167 mmole) was added portion-wise over 120 mins. Following an additional 15 mins of stirring at 0° C., the reaction mixture was poured over ice and the resulting precipitate was isolated by filtration, rinsing with cold $H_2O$. Purification by flash chromatography, eluting with a gradient of 15–50% EtOAc in hexanes, provided 8.14 g (51%) A1 as a white solid. The $^1H$ NMR was consistent with that of the desired structure.

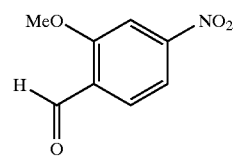

A stirred suspension of A1 (81.94 g, 307 mmole) in dioxane (100 mL) was treated with concentrated HCl (20 mL) and heated at reflux overnight. Upon cooling to ambient temperature, the product A2 precipitated as a light yellow crystalline solid in a yield of 40.65 g (73.1%). The filtrate was concentrated to a volume of ca. 80 mL and a second crop of product crystals was driven from solution by the addition of hexanes, yielding 8.91 g (16.0%). Both batches were identical by $^1H$ NMR and TLC analysis and were consistent with that of the desired material. The total yield of A2 was 49.56 g (89.1%).

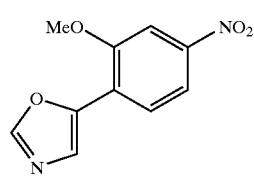

A solution of A2 (456 mg, 2.51 mmole), tosylmethyl isocyanide (490 mg, 2.51 mmole) and $K_2CO_3$ (347 mg, 251 mmole) were dissolved in methanol and heated to reflux for 1.5 hours. The product mixture was then concentrated in vacuo, redissolved in $CH_2Cl_2$, washed with water and brine, dried over $Na_2SO_4$ and again concentrated in vacuo. Purified product A3 was obtained through recrystallization (Et₂O/hexanes) to yield 375 mg (68%). The ¹H NMR was consistent with that of the desired structure.

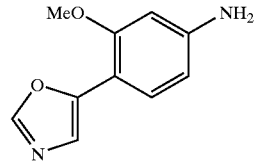

A4

A solution of A3 (4.214 g, 19.1 mmole) in EtOAc (150 mL) was treated with 10% Pd/C (1.05 g, 25 wt. % of A3) and subjected to 40 psi H₂(g) (Parr Hydrogenation Apparatus) overnight. The reaction mixture was filtered and concentrated in vacuo. Pure product A4 was obtained through flash chromatography, eluting with a gradient of 30–40% EtOAc/hexanes, in a yield of 3.4 g (93%). The ¹H NMR was consistent with that of the desired structure.

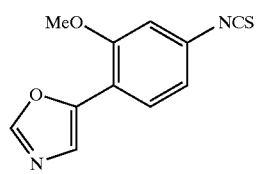

A5

A solution of A4 (250 mg, 1.3 mmoles) in 10 mL of methylene chloride was treated with 1, 1'-thiocarbonyldi-2 (1H)-pyridone (302 mg, 1.3 mmoles). The resulting solution was stirred at room temperature for 10 min., and then washed once with water and once with 0.5 N HCl. The organic layer was dried with sodium sulfate, filtered, and concentrated in vacuo. The resulting oil A5 was used immediately.

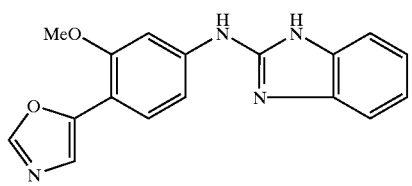

5

Compound A5 (1.3 mmoles) in 44 mL of benzene was treated with phenylene diamine (140 mg, 1.3 mmoles). The resulting solution was heated to reflux for 15 min., at which time 405 mg (1.95 mmoles) of dicyclohexylcarbodiimide was added. Refluxing was continued for 5 h. After cooling to room temperature a precipitate 5 was isolated by filtration (270 mg, 68% for 2 steps). Mass spectral analysis was consistent with that of the desired structure. ¹H NMR (500 MHz, d₆-DMSO) δ11 (s, 1H), 9.7 (s, 1H), 8.3 (s, 1H), 7.65 (d, 2H), 7.55 (d, 1H), 7.4 (s, 1H), 7.3 (bd, 2H), 7.0 (bs, 2H), 3.95 (s, 3H).

EXAMPLE 2

Synthesis of Compound 8

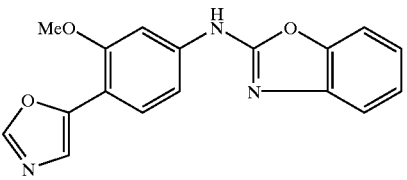

8

A solution of A4 (500 mg, 2.63 mmol) and 2-chlorobenzoxazole (0.2 ml, 1.75 mmol) in DMF (2 mL) was heated to 100° C. and stirred overnight. The reaction mixture was diluted with ethyl acetate and 2N HCl. The layers were partitioned and the organic extracts dried over MgSO₄. The organics were concentrated in vacuo and the residue purified via medium pressure liquid chromatograph (elution with 1:99 MeOH/CH₂Cl₂) to give 54 mgs (13%) of 8 as a light yellow solid; TLC: $R_f$=0.20 (3:97 MeOH/CH₂Cl₂). ¹HNMR (500 MHz, CDCl₃) δ9.2 (bs), 8.0 (s), 7.85 (d), 7.7–7.55 (m), 7.45 (d), 7.35–7.1 (m) 4.15 (s).

EXAMPLE 3

Synthesis of Compound 9

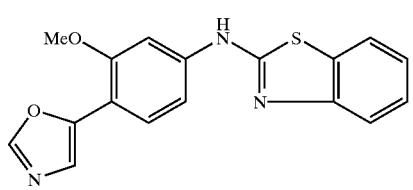

9

A solution of A4 (500 mg, 2.63 mmol) and 2-chlorobenzothiazole (0.2 ml, 1.5 mmol) in DMF (2 mL) was heated to 100° C. and stirred overnight. The reaction mixture was diluted with ethyl acetate and 2N HCl. The layers were partitioned and the organic extracts dried over MgSO₄. The organics were concentrated in vacuo and the residue purified via medium pressure liquid chromatograph (elution with 1:99 MeOH/CH₂Cl₂) to give 176 mgs (41%) of 9 as a light yellow solid; TLC: $R_f$=0.23 (3:97 MeOH/CH₂Cl₂). ¹HNMR (500 MHz, CDCl₃) δ 8.1 (bs), 8.0 (s), 7.85 (d), 7.75 (d), 7.6 (s), 7.5 (s), 7.45 (t), 7.25 (t), 7.15 (d), 4.1 (s).

EXAMPLE 4

Synthesis of Compound 15

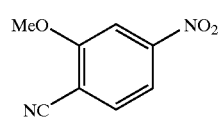

B1

A solution of 2-bromo-5-nitroanisole (1.0 g, 4.3 mmol) and copper(I)cyanide (388 mg, 4.3 mmol) in DMF (5 mL) was heated to 150° C. for four hours. The product mixture was cooled to ambient temperature and poured into water. The resulting precipitate was filtered, dissolved in CH₂Cl₂, dried (MgSO₄) and concentrated to yield a tan solid B1 in a yield of 634 mg(83%). The $^1$H NMR was consistent with that of the desired structure.

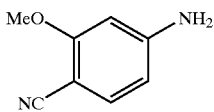
B2

B1 (192 mg, 1.08 mmol) and SnCl$_2$.2H$_2$O (729 mg, 3.23 mmol) were combined in ethanol (5 mL) and heated to 75° C. for a period of one hour. The reaction mixture was cooled to ambient temperature, diluted with ethyl acetate, and washed with saturated NaHCO$_3$ (aq, diluted with 2N NaOH to break emulsion, 2×'s) and water (1×). Dried (MgSO$_4$) and concentrated to yield an orange solid B2 in a yield of 140 mg (88%). The $^1$H NMR was consistent with that of the desired structure.

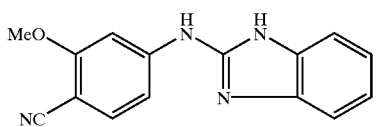
15

Compound 15 was prepared in a fashion analogous to that of compound 5 wherein B2 (50 mg, 0.34 mmol) gave rise to 15 in a yield of 46.5 mg (52%). TLC: R$_f$=0.22 (60% EtOAc in hexanes). $^1$HNMR (500 MHz, CDCl$_3$) δ11.24 (s, 1H), 10.12 (s, 1H), 7.68 (s, 1H), 7.61 (d, 1H), 7.52 (d, 1H), 7.41 (bd, 1H), 7.32 (bd, 1H), 7.05 (m, 2H), 3.92 (s, 3H).

EXAMPLE 5
Synthesis of Compound 25

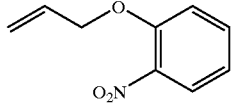
C1

To a solution of 2-nitrophenol (45 mmol) in DMF (10 ml) was aded powdered K$_2$CO$_3$ (56 mmol) and allyl bromide (55 mmol). The mixture was stirred at ambient temperature for one hour, diluted with ether and washed with water (3×s) and brine (1×). The resulting product solution was dried (Na$_2$SO$_4$), and concentrated to yield C1 which was utilized with no further purification.

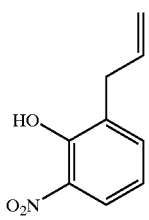
C2

C2 (45 mmol, neat) was heated overnight at 180° C. under nitrogen. Upon cooling to ambient temperature, the crude product mixture was taken up in ether and extracted with 2N NaOH(aq). This aqueous portion was cooled to 0° C., acidified (2N HCl) and extracted with ether. The extracts were washed with brine, dried (Na$_2$SO$_4$), and concentrated to yield C2 (15.5 mmol). The $^1$H NMR was consistent with that of the desired structure.

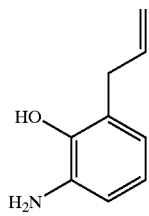
C3

C3 (2.2 mmol) was dissolved in ethanol and treated with iron (powder, 11 mmol) and conc. HCl (1 mL) with heating to reflux overnight. The mixture was cooled to ambient temperature, decanted, basified with NaHCO$_3$ (aq) and extracted with ethyl acetate. The extracts were washed with brine, dried (Na$_2$SO$_4$), and concentrated to provide a brown oil. Purification by silica gel chromatography (eluting with 20% ethyl acetate in hexanes) gave C3 in a yield of 248 mg, 1.2 mmol, 76%) as a dark oil. The $^1$H NMR was consistent with that of the desired structure.

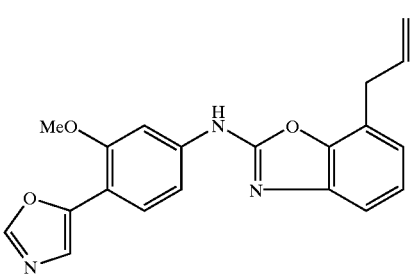
25

Compound 25 was prepared in a fashion analogous to that of compound 5 wherein C3 (78 mg, 0.526 mmol) and A5 (0.53 mmol) gave rise to 25 in a yield of 24 mg (13%). TLC: R$_f$=0.28 (3% CH$_3$OH in CH$_2$Cl$_2$). $^1$HNMR (500 MHz, CDCl$_3$) δ9.73(br s, 1H), 8.11(s, 1H), 7.89(d, 1H), 7.78(d, 1H), 7.54(dd, 1H), 7.47(s, 1H), 7.34(d, 1H), 7.20(t, 1H), 7.00(d, 1H), 6.08(m, 1H), 5.10(m, 2H), 4.08 (s, 3H), 3.60 (d, 2H)

EXAMPLE 6
IMPDH Activity Inhibition Assay

We measured the inhibition constants of the compounds listed in Table II utilizing the following protocol:

IMP dehydrogenase activity was assayed following an adaptation of the method first reported by Magasanik. [Magasanik, B. Moyed, H. S. and Gehring L. B. (1957) J. Biol. Chem. 226, 339]. Enzyme activity was measured spectrophotometrically, by monitoring the increase in absorbance at 340 nm due to the formation of NADH (ε340 is 6220 M$^{-1}$ cm$^{-1}$). The reaction mixture contained 0.1 M Tris pH 8.0, 0.1 M KCl, 3 mM EDTA, 2 mM DTT, 0.1 M IMP and enzyme (IMPDH human type II) at a concentration of 15 to 50 nM. This solution is incubated at 37° C. for 10 minutes. The reaction is started by adding NAD to a final concentration of 0.1M and the initial rate is measured by following the linear increase in absorbance at 340 nm for 10 minutes. For reading in a standard spectrophotometer (path length 1 cm) the final volume in the cuvette is 1.0 ml. The assay has also been adapted to a 96 well microtiter plate format; in this case the concentrations of all the reagents remain the same and the final volume is decreased to 200 μl.

For the analysis of inhibitors, the compound in question is dissolved in DMSO to a final concentration of 20 mM and added to the initial assay mixture for preincubation with the enzyme at a final volume of 2–5% (v/v). The reaction is started by the addition of NAD, and the initial rates measured as above. $K_i$ determinations are made by measuring the initial velocities in the presence of varying amounts of inhibitor and fitting the data using the tight-binding equations of Henderson (Henderson, P. J. F. (1972) Biochem. J. 127, 321].

These results are shown in Table II. $K_i$ values are expressed in nM. Category "A" indicates 0.01 to 500 nm activity, category "B" indicates 501–5,000 nm activity, category "C" indicates 5,001 to 15,000 nm activity, category "D" indicates greater than 15,000 nm activity. The designation "ND" is used where a given compound was not tested.

TABLE II

| Cmpd # | $K_i$ (nM) |
|---|---|
| 1 | ND |
| 2 | D |
| 3 | D |
| 4 | D |
| 5 | B |
| 6 | D |
| 7 | D |
| 8 | A |
| 9 | A |
| 10 | A |
| 11 | B |
| 12 | A |
| 13 | C |
| 14 | A |
| 15 | C |
| 16 | A |
| 17 | A |
| 18 | D |
| 19 | D |
| 20 | D |
| 21 | D |
| 22 | B |
| 23 | B |
| 24 | D |
| 25 | A |

EXAMPLE 15

Anti-Viral Assays

The antiviral efficacy of compounds may be evaluated in various in vitro and in viva assays. For example, compounds may be tested in in vitro viral replication assays. In vitro assays may employ whole cells or isolated cellular components. In vivo assays include animal models for viral diseases. Examples of such animal models include, but are not limited to, rodent models for HBV or HCV, the Woodchuck hepatitis model for HBV, and chimpanzee HCV infection.

While we have described a number of embodiments of this invention, it is apparent that our basic constructions may be altered to provide other embodiments which utilize the products and methods of this invention.

We claim:
1. A compound of the formula:

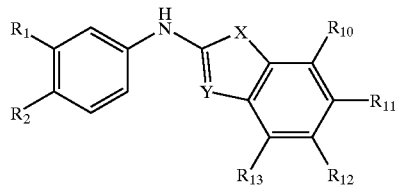

wherein:
$R^1$ and $R^2$ are independently selected from halogen, CN, $NO_2$, $CF_3$, $OCF_3$, OH, $R^3$, $OR^3$, 1,2-methylenedioxy, 1,2-ethylenedioxy, $SR^3$, $S(O)R^3$, $SO_2R^3$, $NH_2$, $NHR^3$, $N(R^3)_2$, $NR^3R^9$, COOH, or $COOR^3$;

each $R^3$ is independently ($C_1$–$C_4$)-straight or branched alkyl, or ($C_2$–$C_4$)-straight or branched alkenyl or alkynyl;

each $R^4$ is independently ($C_1$–$C_6$)-straight or branched alkyl, or ($C_2$–$C_6$)-straight or branched alkenyl or alkynyl; and each $R^4$ optionally comprises up to 2 substituents, wherein:
the first of said substituents, if present, is $R^1$, $R^5$ or $R^8$, and
the second of said substituents, if present, is $R^1$;

each $R^5$ is independently selected from $OR^6$, $OC(O)R^7$, $OC(O)R^6$, $OC(O)OR^7$, $OC(O)OR^6$, $OC(O)N(R^7)_2$, $OP(O)(OR^7)_2$, $SR^7$, $SR^6$, $S(O)R^7$, $S(O)R^6$, $SO_2R^7$, $SO_2R^6$, $SO_2N(R^7)_2$, $SO_2NR^6R^7$, $SO_3R^7$, $C(O)R^6$, $C(O)OR^6$, $C(O)R^7$, $C(O)OR^7$, $NC(O)C(O)R^7$, $NC(O)C(O)R^6$, $NC(O)C(O)OR^7$, $NC(O)C(O)N(R^7)_2$, $C(O)N(R^7)_2$, $C(O)N(OR^7)R^7$, $C(O)N(OR^7)R^6$, $C(NOR^7)R^7$, $C(NOR^7)R^6$, $N(R^7)_2$, $NR^7C(O)R^6$, $NR^7C(O)R^7$, $NR^6C(O)R^6$, $NR^7C(O)OR^7$, $NR^7C(O)OR^6$, $NR^7C(O)N(R^7)_2$, $NR^7C(O)NR^6R^7$, $NR^7SO_2R^7$, $NR^7SO_2R^6$, $NR^7SO_2N(R^7)_2$, $NR^7SO_2NR^6R^7$, $N(OR^7)R^7$, $N(OR^7)R^6$, $P(O)(OR^7)N(R^7)_2$, and $P(O)(OR^7)_2$;

$R^6$ is a monocyclic or a bicyclic ring system consisting of 5 to 6 members per ring, wherein said ring system optionally comprises up to 4 heteroatoms selected from N, O, and S, and wherein a $CH_2$ adjacent to any of said N, O, or S heteroatoms is optionally substituted with C(O); and each $R^6$ optionally comprises up to 3 substituents, each substituent independently selected from $R^1$;

each $R^7$ is independently H, ($C_1$–$C_4$)-straight or branched alkyl, or ($C_2$–$C_4$) straight or branched alkenyl; and each $R^7$ optionally comprises a substituent that is $R^8$;

$R^8$ is a monocyclic or a bicyclic ring system consisting of 5 to 6 members per ring, wherein said ring system optionally comprises up to 4 heteroatoms selected from N, O, and S, and wherein a $CH_2$ adjacent to said N, O or S maybe substituted with C(O); and each $R^8$ optionally comprises up to 2 substituents independently chosen from H, ($C_1$–$C_4$)-straight or branched alkyl, ($C_2$–$C_4$) straight or branched alkenyl, 1,2-methylenedioxy, 1,2-ethylenedioxy and $(CH_2)_n$—Z;

wherein n is 0, 1 or 2;
$R^9$ is an amino protecting group; and
wherein any carbon atom in any $R^3$, $R^4$ or $R^7$ is optionally replaced by O, S, SO, $SO_2$, NH, or N($C_1$–$C_4$)-alkyl,
each $R^{10}$, $R^{11}$, $R^{12}$, and $R^{13}$ is independently selected from hydrogen, $R^1$, and $R^2$,
X is selected from $CH_2$, $CHR^3$, $CHR^4$, O, S, NH, $NR^3$, and $NR^4$, and Y is selected from CH, CR$^3$, CR$^4$, and N, and wherein: when Y is N and R$^{10-13}$ are H, either R$^1$ or R$^2$ is CN, and when Y is N and X is NH, no more than one of R$^1$, R$^2$, R$^{10}$, R$^{11}$, R$^{12}$, and R$^{13}$ may be Cl, Br, or CF$_3$.

2. A pharmaceutical composition comprising:
 a. a compound according to claim 1 in an amount effective to inhibit IMPDH activity; and
 b. a pharmaceutically acceptable adjuvant.

3. The pharmaceutical composition according to claim 2, additionally comprising an additional agent selected from an immunosuppressant, anticancer agent, antiviral agent, antiinflammatory agent, antifungal agent, antibiotic, or antivascular hyperproliferation agent.

4. A method of inhibiting IMPDH activity in a mammal comprising the step of administering to said mammal a compound according to claim 1.

5. A method for treating or preventing IMPDH mediated disease in a mammal comprising the step of administering to said mammal a composition according to claim 2.

6. The method according to claim 5, wherein said composition additionally comprises an agent selected from an immunosuppressant, anticancer agent, antiviral agent, antiinflammatory agent, antifungal agent, antibiotic, or antivascular hyperproliferation agent.

7. The method according to claim 5 or 6, wherein said method is used to suppress an immune response and wherein said additional agent, if present, is an immunosuppressant.

8. The method according to claim 7, wherein said IMPDH mediated disease is an autoimmune disease.

9. The method according to claim 5 or 6, wherein the IMPDH mediated disease is a viral disease and wherein said additional agent, if present, is an antiviral agent.

10. The method according to claim 5 or 6, wherein the IMPDH mediated disease is a vascular disease and wherein said additional agent, if present, is an antivascular hyperproliferation agent.

11. The method according to claim 5 or 6, wherein the IMPDH mediated disease is cancer and wherein said additional agent, if present, is an anticancer agent.

12. The method according to claim 5 or 6, wherein the IMPDH mediated disease is an antunflammatory disease and wherein said additional agent, if present, is an antiinflammatory agent.

* * * * *

UNITED STATES PATENT AND TRADEMARK OFFICE
CERTIFICATE OF CORRECTION

PATENT NO. : 6,518,291 B1
DATED : February 11, 2003
INVENTOR(S) : Jeffrey O. Saunders et al.

It is certified that error appears in the above-identified patent and that said Letters Patent is hereby corrected as shown below:

Title page,
Item [56], OTHER PUBLICATIONS, change "*Transplatation*" to -- *Transplantation* --.
Item [57], ABSTRACT,
Line 6, change "consequently, may be" to -- consequently may be --.

Column 1,
Lines 38, 58 and 62, change "et." to -- et --.

Column 2,
Lines 2, 3, 24, 41, 44, 51 and 54, change "et." to -- et --.

Column 3,
Line 3, change "et." to -- et --.

Column 4,
Line 42, change "of using them of this invention" to -- for using them of this invention --.

Column 5,
Line 28, change "hydrogen halogen" to -- hydrogen, halogen --.
Line 39, change "ranched" to -- branched --.

Column 6,
Line 11, change "maybe" to -- may be --.
Line 63, change "heteroatom" to -- heteroatoms --.

Column 15,
Line 19, change "sions Other" to -- sions. Other --.
Line 35, change "may be suspended or dissolved in an oily phase is" to -- , which may be suspended or dissolved in an oily phase, is --.

Column 17,
Line 36, change "including," to -- including --.
Line 45, change "Gravels disease" to -- Graves' disease --.

UNITED STATES PATENT AND TRADEMARK OFFICE
CERTIFICATE OF CORRECTION

PATENT NO.    : 6,518,291 B1
DATED         : February 11, 2003
INVENTOR(S)   : Jeffrey O. Saunders et al.

It is certified that error appears in the above-identified patent and that said Letters Patent is hereby corrected as shown below:

Column 18,
Lines 20, 38 and 54, change "including," to -- including --.

Column 23,
Line 44, change "aded" to -- added --.

Column 25,
Line 55, change "in viva" to -- in vivo --.

Column 26,
Line 54, change "maybe" to -- may be --.

Column 28,
Line 19, change "antunflammatory" to -- antiinflammatory --.

Signed and Sealed this

Twenty-third Day of September, 2003

JAMES E. ROGAN
*Director of the United States Patent and Trademark Office*